United States Patent
Attrill et al.

(10) Patent No.: US 9,000,090 B2
(45) Date of Patent: Apr. 7, 2015

(54) POLYISOPRENE CONDOMS

(75) Inventors: Julie Attrill, London (GB); Melissa Jane Ballard, London (GB); Eman Alsaffar, London (GB)

(73) Assignee: LRC Products Limited, Slough, Berkshire (GB)

( * ) Notice: Subject to any disclaimer, the term of this patent is extended or adjusted under 35 U.S.C. 154(b) by 1354 days.

(21) Appl. No.: 12/294,520

(22) PCT Filed: Mar. 12, 2007

(86) PCT No.: PCT/GB2007/000842
§ 371 (c)(1),
(2), (4) Date: Jun. 24, 2010

(87) PCT Pub. No.: WO2007/113463
PCT Pub. Date: Oct. 11, 2007

(65) Prior Publication Data
US 2010/0267917 A1  Oct. 21, 2010

(30) Foreign Application Priority Data
Mar. 31, 2006  (GB) .................................. 0606536.1

(51) Int. Cl.
| | | |
|---|---|---|
| *C09J 179/00* | (2006.01) | |
| *C09J 165/00* | (2006.01) | |
| *C09J 7/02* | (2006.01) | |
| *A61F 6/04* | (2006.01) | |
| *B29C 41/00* | (2006.01) | |
| *C08C 1/00* | (2006.01) | |
| *C08C 1/02* | (2006.01) | |
| *C08J 3/24* | (2006.01) | |
| *C08K 5/00* | (2006.01) | |
| *C08K 5/39* | (2006.01) | |

(52) U.S. Cl.
CPC ................. *A61F 6/04* (2013.01); *B29C 41/003* (2013.01); *C08C 1/00* (2013.01); *C08C 1/02* (2013.01); *C08J 3/241* (2013.01); *C08J 2309/10* (2013.01); *C08K 5/0025* (2013.01); *C08K 5/39* (2013.01)

(58) Field of Classification Search
None
See application file for complete search history.

(56) References Cited

U.S. PATENT DOCUMENTS

| | | | |
|---|---|---|---|
| 3,215,649 A | 11/1965 | Preiss et al. | |
| 3,917,746 A | 11/1975 | Aishima et al. | |
| 5,407,715 A * | 4/1995 | Buddenhagen et al. | 428/35.7 |
| 6,187,857 B1* | 2/2001 | Ozawa et al. | 524/565 |
| 6,329,444 B1 | 12/2001 | McGlothlin et al. | |
| 6,618,861 B2 | 9/2003 | Saks et al. | |
| 6,639,007 B2* | 10/2003 | Plamthottam | 524/571 |
| 6,828,387 B2* | 12/2004 | Wang et al. | 525/329.3 |
| 7,294,678 B2* | 11/2007 | McGlothlin et al. | 525/331.9 |
| 7,374,711 B2* | 5/2008 | McGlothlin et al. | 264/301 |
| 2002/0173563 A1 | 11/2002 | Wang et al. | |
| 2004/0071909 A1* | 4/2004 | McGlothlin et al. | 428/36.8 |

FOREIGN PATENT DOCUMENTS

| | | |
|---|---|---|
| EP | 1 362 566 | 11/2003 |
| SU | 706425 A1 | 12/1979 |
| WO | WO 02/090430 A1 | 11/2002 |
| WO | WO 03/072340 A1 | 9/2003 |
| WO | 2006081415 A2 | 8/2006 |
| WO | WO 2006/081415 A2 | 8/2006 |
| WO | 2007017368 A1 | 2/2007 |
| WO | 2007017375 A1 | 2/2007 |

OTHER PUBLICATIONS

"Product Testing & Calibration Unit." Malaysian Rubber Board. Sep. 24, 2008 <http://www.lgm.gov.my/services/rptu/rrimrelax.html>.
UKIPO Examination Reports dated Dec. 1, 2010 and Jun. 23, 2011 for GB2436566.
Applicant's Aug. 18, 2011 Response to UKIPO Examination Reports for GB2436566, including clean and marked up copies of changes to Specification and Claims.

* cited by examiner

*Primary Examiner* — James J Seidleck
*Assistant Examiner* — Peter A Salamon
(74) *Attorney, Agent, or Firm* — Troutman Sanders, LLP; Ryan A. Schneider; Elizabeth-Ann Weeks

(57) ABSTRACT

The present invention relates to processes for making synthetic polyisoprene latex and synthetic polyisoprene condoms. A process for making a compounded synthetic polyisoprene latex suitable for making a latex film comprises (a) compounding a synthetic polyisoprene latex with suitable compounding ingredients, (b) maturing the latex and optionally (c) storing the latex; characterized in that steps (a), (b) and (c) if included are carried out at a low temperature so as to minimize prevulcanization of the latex. Condoms can be made from latexes produced according to the process of the invention.

28 Claims, No Drawings

POLYISOPRENE CONDOMS

This application is a National Stage Application of PCT/GB2007/000842, filed Mar. 12, 2007, which claims benefit of Serial No. 0606536.1, filed Mar. 31, 2006 in Great Britain and which application(s) are incorporated herein by reference. To the extent appropriate, a claim of priority is made to each of the above disclosed applications.

The present invention relates to processes for making synthetic polyisoprene latex and synthetic polyisoprene condoms, and to condoms obtained from such processes.

Natural rubber, which is comprised primarily of cis-1,4-polyisoprene, has been used extensively as a material for the construction of dip-moulded objects, such as surgical gloves, balloons, condoms, and the like. However, articles formed from natural rubber latex are associated with a number of health problems. Some users experience allergic reactions, or other adverse reactions (such as irritant dermatitis) to natural rubber (more specifically, to proteins remaining in the natural rubber, or to chemicals added to promote curing of the film), which may result in painful or unpleasant symptoms.

Various synthetic elastomers have been used as substitutes for natural rubber. Nitrile and chloroprene synthetic rubber materials, for example, have been used in the manufacture of surgical gloves and examination glove. However, these materials do not have the high resiliency and low tensile set values (resiliency) of natural rubber. Polyurethane has also been used as a natural rubber substitute but although polyurethanes have very high tensile strength, they lack the resiliency and low tensile set values of natural rubber. As a result, polyurethanes have been found to be unsuitable for many applications of natural rubber.

Development of a true replacement for natural rubber has proved difficult, with synthetic variants typically having, for example, different molecular weight characteristics to natural rubber. This has, in turn, resulted in synthetic polyisoprene films having an inferior balance of properties compared to those of a vulcanised natural rubber film.

In particular, in attempts to employ cis-1,4-polyisoprene (the main component of natural rubber) without the protein that is retained from natural rubber sources, it has been found that the resulting dip-moulded products, in particular condoms, lack the tensile characteristics that are an important feature of these devices, and may be less mechanically strong. For example, U.S. Pat. No. 3,917,746 recognises that products formed from unmodified cis-1,4-polyisoprene are deformed on removal of the cured article from the mould, and contain streaks and grooves in the rubber film, which cause mechanical deficiencies.

Various documents describe attempts to improve the tensile strength of synthetic polyisoprene rubber by increasing the cross-linking of the polyisoprene rubber used.

U.S. Pat. No. 3,215,649 discloses polyisoprene rubber lattices that can be cured using sulphur and zinc alkyldithiocarbamates and zinc mercaptobenzothiazole with zinc oxide as an activator. The latex is prevulcanised at 40° C. or 50° C. to a suitable crosslink density—for 72 hours at 40° C. or 16 hours at 50° C. This time can be reduced using higher temperatures but above 65°-70° C. is not recommended as the latex starts to degrade. The maximum tensile strength value given is 460 psi (about 3 MPa), which is inadequate for a condom.

U.S. Pat. No. 6,329,444 discloses devices made from polyisoprene rubber latex dipping, but without the use of sulphur-containing components. In general, they use peroxides and high temperatures or high-energy radiation. Curing with peroxides requires oxygen to be excluded from the system during curing, and entails immersing the polyisoprene rubber latex in a molten salt bath (eg at 180° C.). This technique precludes the use of a conventional latex condom dipping line, so it is not suitable for manufacturing condoms.

U.S. Pat. No. 6,618,861 discloses a method of making gloves having a clear wrist portion, from a range of materials including polyisoprene rubber latex. The process details given are limited but a formulation is given for polyisoprene rubber latex in Example 2 that includes five accelerators (tetramethylthiuram disulphide, zinc 2-mercaptobenzothiazole, zinc dibutyldithiocarbamate, zinc diethyldithiocarbamate and 1,2-diphenyl-2-thiourea), as well as sulphur and zinc oxide as vulcanising agents. The tensile properties of films made from this polyisoprene rubber latex are given as tensile strength 13.22 MPa, elongation-at-break 1028%, and stress at 300% strain 1.03 MPa. The tensile strength obtainable by this process is inadequate for a condom. There is essentially no teaching concerning the process parameters.

WO 02/090430 discloses a process for making polyisoprene articles, using a novel three-part accelerator system comprising a dithiocarbamate, a thiazole and a guanidine compound. There is specific teaching that omission of any of the three preferred accelerator components results in significantly decreased tensile strength: use of the three-part accelerator system is thus taught as essential. The process comprises a prevulcanisation step after compounding, which requires heating to above 20° C., preferably 25 to 30° C., and dipping is also carried out at temperatures of 20° C. or above. Pre-cure temperatures of 20° C. give poor tensile strength values (equivalent to 15-17 MPa) suggesting that higher temperatures should be used. The highest reported tensile strength value obtained using the claimed process is 3939 psi (equivalent to 27.2 MPa), after storing for 6 days at ambient temperature. Higher tensile strengths are desirable for condoms.

WO 03/072340 discloses condoms made from polyisoprene rubber latex cured using accelerators selected from one or more of diisopropyl xanthogen polysulphide, tetraethylthiuram disulphide and zinc diethyldithiocarbamate. The specification refers to a prior art polyisoprene article made using a combination of sulphur, zinc oxide and dithiocarbamate as a curing package. However, the latex is stated as showing poor shelf-stability, coagulating within a few days of compounding.

There is a stated need for a condom that shows no deterioration in physical properties on ageing, and condoms that show no deterioration in properties upon maturation of the compounded polyisoprene rubber latex. No data are provided in the specification to show that the claimed formulation provides these properties; indeed no data are provided on the effect of ageing of the condom or the latex.

The specification further states that conventional accelerator systems (presumably those not containing xanthates), which use zinc dithiocarbamates such as zinc dibenzyldithiocarbamate, give significantly shortened acceptable dipping life for the polyisoprene rubber latex.

The process parameters given require the first dip to be dried at 60° C. for 3-4 minutes, cooled to RT or below, and then the second dip is dried at 60° C. for 3-4 minutes, the bead formed, the condom leached at 60° C. or higher for 1 min and then cured at 300° C. [sic] for 5 minutes before a final leach at 60°-65° C. for 1 min. The initial latex is stated (Table 2) to have a temperature of 77° F. (25° C.).

U.S. Pat. No. 6,828,387 discloses a process for making articles from polyisoprene rubber latex. It uses a three-part accelerator system comprising a dithiocarbamate, a thiazole and a guanidine, and states that the compounded latex exhibits prolonged storage stability of up to 8 days compared with typical 3-5 days for polyisoprene rubber latex.

There is an initial precure processing performed at less than 35° C. for 90-150 minutes and the compounded latex can be stored for up to 8 days at 15° C.-20° C. In the examples, the latex is compounded at a temperature of 25° C. and maintained at a temperature below 25° C. Glove formers, with a coagulant-coating, are dipped into the compounded polyisoprene rubber latex at ambient or a temperature between 20°-25° C., heated at 70° C. for 1 minute then leached at 65° C. for 5 minutes, then dried at 70° C. for 5 minutes before final curing at 120° C. for about 20 minutes.

In all previously described processes, some degree of prevulcanisation is introduced into the latex. We have now found that even low levels of prevulcanisation can have a significant adverse impact on the physical properties of the products made. Having appreciated this problem, we have now devised a way of substantially overcoming or minimising it.

According to a first aspect of the present invention, there is provided a process for making a compounded synthetic polyisoprene latex suitable for making a Mtex film, which process comprises (a) compounding a synthetic polyisoprene latex with suitable compounding ingredients, (b) maturing the latex and optionally (c) storing the latex; characterised in that steps (a), (b) and (c) if included are carried out at low temperature so as to minimise prevulcanisation of the latex. The invention also includes making thin-film articles, in particular, condoms from the compounded latex so provided.

There is also provided, in a second aspect, a process for making a synthetic polyisoprene condom, which process comprises dipping a suitably shaped former into a compounded synthetic polyisoprene latex and vulcanising the latex to form a condom, characterised in that during preparation and optional storage the latex is maintained at low temperature so as to minimise prevulcanisation of the latex. Preparation of the latex is suitably in accordance with the first aspect of the invention.

We have found that the drawbacks of the prior art processes outlined above can, surprisingly, be overcome or substantially reduced by controlling the amount of prevulcanisation of the latex to very low levels. We have found this can be achieved by cooling the latex to a temperature such that very little, or substantially no, prevulcanisation occurs. "Low temperature" refers to temperatures at which very low levels of prevulcanisation occur, and will typically be several degrees ° C. below ambient or room temperature (25° C.), for example, we prefer to use temperatures below 20° C.

It is preferred to maintain or cool the latex to a temperature of about 17° C. or less, more preferably 15° C. or less. Temperatures of around 15° C.±2° C. are particularly preferred.

We have found that latex films, in particular condoms, produced from latex having a very low level of prevulcanisation possess a number of advantageous characteristics. The cured films possess better burst properties—in terms of the volume and pressure at burst; and superior tensile properties, and these properties are retained after ageing even at temperatures of up to 70° C. These characteristics are shown by both lubricated and dry condoms. The present invention also results in minimal film defects such as "mud cracking" and minimises non-uniform flow of the latex which can lead to undesirable variations in film thickness.

Suitably, the synthetic polyisoprene latex is maintained at low temperature, in particular about 15° C.±2° C., during all preliminary stages of the process—that is, during compounding of the latex, maturation, storage in the reserve tanks, transfer to the dipping line and so far as possible during dipping, up until the point of vulcanisation.

Accordingly, a third aspect of the present invention provides a process for making a compounded synthetic polyisoprene latex suitable for making a latex film, which process comprises (a) compounding a synthetic polyisoprene latex with suitable compounding ingredients, (b) maturing the latex and optionally (c) storing the latex; characterised in that steps (a), (b) and (c) if included are carried out below 20° C., preferably at about 17° C. or less, suitably at about 15° C.±2° C.

There is also provided, in a fourth aspect, a process for making a synthetic polyisoprene condom, which process comprises dipping a suitably shaped former into a compounded synthetic polyisoprene latex and vulcanising the latex to form the condom, characterised in that during preparation, and optional storage, the latex is maintained at below 20° C., preferably at about 17° C. or less, suitably at about 15° C.±2° C.

One measure of the amount of prevulcanisation in the latex is the crosslink density, and this can be determined, for example, by a prevulcanisate relaxed modulus measurement (PRM). The method for measuring relaxed modulus is based upon an original method devised by Gorton and Pendle (Natural Rubber Technology, 1976, 7(4), 77-81). Measurement of the relaxed modulus of films cast from prevulcanisate provides a reproducible indication of the state of vulcanisation in the film—that is, of the film's crosslink density. PRM can be determined using the following procedure:

1. Ensure the latex has been stirred
2. Take a round-ended tube such as a boiling tube (of known circumference, C centimeters), dip it into the latex and withdraw slowly and steadily
3. Allow the excess latex to run off and place the tube in an oven at 70° C. for 2.5 minutes
4. Wipe off the excess latex at the lip of the open end of the tube with tissue
5. Roll the latex film up the length of the tube from the open end to form a ring and remove the ring from the tube.
6. Weigh the ring on an analytical balance to find its mass (M grams)
7. Place the ring on suitable mounts on a tensile tester and stretch the ring to 100% extension and hold.
8. After one minute measure the load in Newtons exerted by the ring.
9. Using the load reading and the mass of the ring, calculate the PRM (in Mega Pascals) as follows:

$$PRM(MPa) = \frac{F \times d \times C}{2M}$$

where:
F=load (N) exerted by the ring after one minute at 100% extension
d=density of the latex ring (g·cm$^{-3}$)
C=external circumference of dipping tube (cm)
M=mass of latex ring (g)

Typically, the PRM is measured on four samples and the mean recorded. The testing can be carried out using, for example, the RRIM Relaxed Modulus Tester, Model M403, available from the Malaysian Rubber Board (see www.lgm.gov.my/services/rptu/rrimrelax.html).

Suitably, the PRM of the latex should be no more than about 0.1 MPa Minimising prevulcanisation of the latex essentially refers to keeping the PRM (and by implication, crosslink density) substantially at this level or below.

A PRM value of from about 0.08 to about 0.10 MPa is preferred, so latexes having this property are particularly suitable. The maturation time of the compounded latex can be adjusted accordingly so as to give the desired PRM (crosslink density).

Thus, there is also provided in a fifth aspect of the invention, a process for making a compounded synthetic polyisoprene latex suitable for making a latex film, which process comprises (a) compounding a synthetic polyisoprene latex with suitable compounding ingredients, (b) maturing the latex and optionally (c) storing the latex; characterised in that steps (a), (b) and (c) if included are carried out at low temperature such that the PRM of the latex is about 0.1 MPa or less.

A sixth aspect of the invention also provides a process for making a synthetic polyisoprene condom, which process comprises dipping a suitably shaped former into a compounded synthetic polyisoprene latex and vulcanising the latex to form the condom, characterised in that during preparation and optional storage the latex is maintained at low temperature such that the PRM of the latex is about 0.1 MPa or less.

The invention also provides a condom obtainable by the processes of the second, fourth and sixth aspects of the invention, and also provides latex film articles, in particular condoms, obtainable from the compounded synthetic polyisoprene latex provided by the first, third and fifth aspects of the invention. The invention thus encompasses the use of the compounded latexes provided herein for making latex film articles, particularly condoms.

By way of background, there are three basic compounding approaches to making latex films.

a) Unvulcanised latex

The latex is compounded (ie the chemicals that will effect cure are blended into the latex) without any heating, and the latex then added to the dipping plant, the product dipped and finally vulcanised [=cured] on-plant.

b) Partly prevulcanised latex

The latex is compounded and prevulcanised at elevated temperature, allowed to mature and then compounded further if necessary before being added to the dipping plant, product dipped and vulcanisation completed. This is the commonest approach.

c) Fully prevulcanised latex

The latex is compounded and fully vulcanised off-plant. It is then added to the dipping plant and product dipped. No, or only limited, vulcanisation takes place on the plant.

All of the above can be "straight dipping", where no coagulant of the latex is used, or "coagulant dipping" where a dip into a coagulant precedes the latex dipping. Straight dipping is in general used for the manufacture of thin-walled products such as condoms, whereas coagulant dipping is used to manufacture thicker products such as gloves.

A typical prevulcanisation process for Natural Rubber latex (NRL) will entail:

1) prevulcanisation—the compounding ingredients are added to the NRL, and the latex heated with stirring, to 60° C.±2° C. and maintained at this temperature for 14 hours;
2) maturation—the latex is cooled to ambient and additional vulcanisation activator added (if necessary) and the latex allowed to mature at ambient for six to ten days;
3) reserve (or final stage compounding)—further vulcanisation activator is added if necessary, and the latex heated at 40° C.±2° C. for 18 hours;
4) transfer—the latex is cooled to ambient, the viscosity adjusted and the latex transferred to dip tanks on the plant;
5) dipping—the latex in the dip tanks is maintained at ambient (typically>20° C.).

As noted above, certain prior art also describes articles made from synthetic polyisoprene latex, or methods for making them, and in each case matures the compounded latex to introduce some degree of prevulcanisation into it. We have found that introducing even low levels of prevulcanisation before dipping can impact significantly on the products made, such that they have inadequate physical properties or the properties degrade rapidly upon high temperature ageing or long term storage. Further, prevulcanisation can affect adversely the film-forming properties of the polyisoprene latex.

The starting materials for the present process are all readily available commercially, and may be obtained from any suitable source. For example, raw polyisoprene latex may be obtained from Kraton Corporation, Houston, Tex.

As will be understood in the art, the raw latex must be compounded with suitable compounding ingredients so as to give a latex which can subsequently be cured to provide a latex film. A generalised, typical compounded latex formulation is as follows:

TABLE 1 latex formulation

| Ingredient Function | pphr[1] |
|---|---|
| Synthetic polyisoprene latex | 100 |
| Stabilisers | 0-9[2] |
| pH adjuster | 0-0.1 |
| Vulcanising agent | 0.6-1.0 |
| Vulcanising activator | 0.1-0.4 |
| Accelerator | 0.5-1.0 |
| Antidegradant | 0.5-1.5 |
| Water | 0-20 |

[1]pphr = parts per hundred rubber
[2]stabilisers - may comprise a number of separate compounds The above formulation is given for illustration only, it being understood that in principle any suitably compounded synthetic polyisoprene latex may be used. It should be noted that whilst polyisoprene is the major (or only) rubber polymer, the invention does not exclude the presence of small amounts of other suitable copolymers.

Any suitable accelerator or combination of accelerators can be used in the formulation. However, we have found that when the compounding, maturing and optionally storage steps of the process for making a compounded synthetic polyisoprene latex are carried out at a low temperature, so as to minimise prevulcanisation of the latex, it is possible to use a single accelerator. Accordingly, it is preferred to use a single accelerator rather than a combination. For example, the single accelerator is suitably a dithiocarbamate, preferably zinc dibutyldithiocarbamate. It is preferred not to use thiazoles or guandines.

The compounding step comprises blending the raw latex with the desired compounding ingredients, and can be carried out in any suitable vessel in which the temperature of the latex can be controlled. During compounding, the latex is suitably maintained at about 17° C. or less, preferably at about 15° C.±2° C. so as to minimise any prevulcanisation. Any suitable compounding ingredients may be used—those skilled in the art are well aware of suitable compounds which may be employed.

After compounding, the latex will typically be matured. For example, this will typically involve storage of the compounded latex for a period of time, prior to transfer to the dipping tanks. Preferably, the maturation time is minimal. A suitable period is about 24-48 hours. The maturation time is governed by the development of crosslink density in the latex. It is preferred for the maturation time to be no longer than results in a PRM of about 0.1 MPa or less, more preferably 0.08-0.1 MPa, although the PRM may be lower than this range if desired. The maturation should be done at low temperature, preferably at below 20° C., more preferably at about 17° C. or below, even more preferably about 15° C.±2° C., for example for a period of 24 to 48 hours.

Minimal crosslinking/maturation of the latex enables correct adjustment of the rheology of the latex and helps prevent defects, such as "mud cracking" and non-uniform flow—the latter leading to thickness variations in the film.

Conventional crosslink density measurement typically requires a disc of a specified diameter to be cut from the latex film. This is then placed in a solvent such as toluene or n-heptane, which causes the film to swell; the diameter of the disc is measured when the swelling equilibrates, and the final and initial diameters are used to calculate a "swelling index". However, the films of the present invention all disintegrate when swollen in these hydrocarbon solvents, demonstrating the extremely low level of crosslink density in them. The prior art that describes crosslink density measurement invariably shows swelling of the film samples in a solvent, thus demonstrating that they have developed a significantly higher level of crosslinking than the films made in accordance with the present invention.

After maturation of the compounded latex, it may optionally be transferred to a reserve or storage tank before being transferred to a dipping tank where dipping of shaped mandrels into the latex occurs. Any storage of the compounded latex should be done at low temperature, preferably at the temperatures indicated above for compounding and maturing. Essentially, up until vulcanisation of the compounded latex on the mandrels, it is highly preferred to maintain the latex at low temperature so as to avoid any further prevulcanisation once the maximum level has been reached. Preferably, during all stages up until vulcanisation, the latex is maintained at about 15° C.±2° C.

Once the matured latex has been transferred to the dipping tanks, it is preferred to begin product dipping as soon as possible so as to avoid any further maturation. The temperature in the dipping tanks is preferably about 15° C. or, more preferably, less than 15° C.

Straight dipping—that is, using no coagulation of the latex, is preferred. Any suitable number of dips may be used, but we prefer to dip at least twice (ie double dipping) into the latex. After the first dip, the mandrels with their films are preferably dried, for example by passing them through a drying oven. Subsequently, they are then preferably cooled, for example by passing them through a refrigeration unit, preferably to about 15° C.±2° C., before further dipping. This prevents any heating of the latex in the second dip tank. This cooling step may be repeated prior to any subsequent dips.

After dipping and drying, postvulcanisation of the film may be effected according to conventional curing techniques. For example, the films may be heated for a period of time at elevated temperature—typically 10 minutes at 120-130° C.

The present processes enable the manufacture of high quality condoms having superior physical properties, whilst still employing conventional systems—for example, a conventional accelerator system can be used.

The following tables illustrate the superior properties of the condoms of the present invention:

TABLE 2 comparison of film properties of lubricated condoms resulting from pre- and post-vulcanised latex.

| Property [for lubricated condoms] | | Natural Rubber Latex | Pre-vulcanised polyisoprene rubber latex | Post-vulcanised polyisoprene rubber latex |
|---|---|---|---|---|
| Tensile strength, MPa | Initial | 22 | 16 | 28 |
| | 7 days @ 70° C. | 26 | — | 25 |
| | 3 months @ 50° C. | 23 | — | 26 |
| Elongation-at-break, % | Initial | 800 | 1020 | 1040 |
| | 7 days @ 70° C. | 810 | — | 1040 |
| | 3 months @ 50° C. | 780 | — | 1030 |
| Stress at 300% strain, MPa | Initial | 1.2 | 1.1 | 1.1 |
| | 7 days @ 70° C. | 1.2 | — | 1.0 |
| | 3 months @ 50° C. | 1.2 | — | 1.0 |
| Burst Volume, dm$^3$ | Initial | 39 | 48 | 49 |
| | 7 days @ 70° C. | 36 | 42 | 46 |
| | 3 months @ 50° C. | 33 | — | 44 |
| Burst Pressure kPa | Initial | 1.8 | 1.2 | 1.5 |
| | 7 days @ 70° C. | 1.7 | 1.1 | 1.4 |
| | 3 months @ 50° C. | 1.8 | — | 1.4 |

The "post-vulcanised" polyisoprene latex has been subjected to minimal prevulcanisation, as described in Example 3. The superior properties of the resulting condom are clearly evident.

Accordingly, the invention also provides a synthetic polyisoprene condom having superior physical properties. In particular, the invention provides a synthetic polyisoprene condom having an initial tensile strength of 24 MPa or above, or a tensile strength of 23 MPa or above after ageing for 7 days at 70° C., or a tensile strength of 20 MPa or above after ageing for 3 months at 50° C. Alternatively, but preferably in addition, the condom also has an initial burst pressure of 1.3 kPa or above, or a burst pressure of 1.2 kPa or above after ageing for 7 days at 70° C., or a burst pressure of 1.4 kPa or above after ageing for 3 months at 50° C. Alternatively, but preferably in addition, the condom also has an initial burst volume of 44 dm$^3$ or above, or a burst volume of 41 dm$^3$ or above after 7 days ageing at 70° C., or a burst volume of 42 dm$^3$ after ageing for 3 months at 50° C. or above. Alternatively, but preferably in addition, the condom has an initial elongation-at break value of 1000% or above, or an elongation-at-break value of 1000% after ageing for 7 days at 70° C. or for 3 months at 50° C. Preferably, the condom has at least two or three of the tensile strength, burst pressure, burst volume and elongation at break properties referred to above. More preferably, all four of the properties as defined are present.

TABLE 3

Film properties of fully packaged lubricated condoms from continuous production

| Synthetic polyisoprene Property | Property minima for foiled condoms | | |
|---|---|---|---|
| | Initial | After 6 months at 50° C. | After 28 days at 70° C. |
| Tensile strength, MPa | 30 | 27 | 23 |
| Elongated-at-break, % | 1,000 | 1,000 | 1,000 |
| Burst pressure, kPa | 1.7 | 1.5 | 1.3 |
| Burst volume, dm$^3$ | 55 | 45 | 55 |

The data in Table 3 demonstrates the stability of condoms produced in accordance with the process of the invention and stored fully packaged at 30° C. and 50° C. respectively. The superior properties of the condoms are clearly apparent.

Accordingly, in one embodiment the invention also provides a synthetic polyisoprene condom comprising one or more physical properties selected from (a) an initial tensile strength of 30 MPa or above, or a tensile strength of 23 MPa or above after ageing for 28 days at 70° C., or a tensile strength of 27 MPa or above after ageing for 6 months at 50° C.;

(b) an initial burst pressure of 1.7 kPa or above, or a burst pressure of 1.3 kPa or above after ageing for 28 days at 70° C., or a burst pressure of 1.5 kPa or above after ageing for 6 months at 50° C.;

(c) an initial burst volume of 55 dm$^3$ or above, or a burst volume of 55 dm$^3$ or above after 28 days ageing at 70° C., or a burst volume of 45 dm$^3$ or above after ageing for 6 months at 50° C. or above; or (d) an initial elongation-at break value of 1000% or above, or an elongation-at-break value of 1000% or above after ageing for 28 days at 70° C. or for 6 months at 50° C.

Preferably, the condom has at least two or three of the tensile strength (a), burst pressure (b), burst volume (c), and elongation at break (d) properties referred to above. For example, the condom can have properties (a) and (b) as defined above, or the condom can have properties (a) and (c), or the condom can have properties (a) and (d), or the condom can have properties (b) and (c), or the condom can have properties (b) and (d) or the properties (c) and (d) as defined above. More preferably, the condom can have three of the properties defined above, for example the condom can have properties (a), (b) and (c) as defined above, or properties (a), (b) and (d) as defined above, or properties (b), (c) and (d) as defined above, or the condom can have the properties (a), (c) and (d) referred to above. Even more preferably, all four of the properties (a), (b), (c) and (d) as defined above are present.

The following Examples illustrate the invention:

EXAMPLE 1

A typical formulation is as follows:

| Ingredient function | pphr[1] Range | Ingredient | Available from |
|---|---|---|---|
| Polyisoprene rubber latex | 100 | Kraton IR-401 | Kraton Corp, Texas |
| Stabilisers | 0-0.5 | Dehydol TA20[2] | Henkel Performance Chemicals, UK |
| | 0-0.3 | Potassium oleate | Kao Corp. SA, Spain |
| | 0-0.1 | Anilan NC30[3] | Anikem Ltd, UK |
| pH adjuster | 0-0.1 | 5% Potassium hydroxide | |
| Vulcanising agent | 0.6-1.0 | Sulphur | |
| Vulcanising activator | 0.1-0.4 | Zinc Oxide | |
| Accelerator | 0.5-1.0 | Zinc dibutyl-dithiocarbamate | As Robac ZDBC from Robinsons Brothers Ltd, UK |
| Antidegradant | 0.5-1.5 | Struktol LA229[4] | Schill & Seilacher Group, Germany |
| — | 0-20 | Water | |

[1]parts per hundred rubber
[2]cetylstearate/ethylene oxide condensate
[3]sodium alkyl benzene sulphonate
[4]aqueous dispersion of butylated reaction by-product of p-cresol and dicylcopentadiene

EXAMPLE 2

A specific example of a formulation according to Example 1 is as follows:

| Ingredient function | pphr[1] | Ingredient |
|---|---|---|
| Polyisoprene rubber latex | 100 | Kraton IR-401 |
| Stabilisers | 0.4 | Dehydol TA20[2] |
| | 0.3 | Potassium oleate |
| | 0.1 | Anilan NC30 |
| pH adjuster | 0.1 | 5% Potassium hydroxide |
| Vulcanising agent | 0.8 | Sulphur |
| Vulcanising activator | 0.2 | Zinc Oxide |
| Accelerator | 0.8 | Zinc dibutyldithiocarbamate |
| Antidegradant | 1.0 | Struktol LA229[4] |
| — | 7.4 | Water |

[1]parts per hundred rubber
[2]cetylstearate/ethylene oxide condensate
[3]sodium alkyl benzene sulphonate
[4]aqueous dispersion of butylated reaction by-product of p-cresol and dicylcopentadiene

EXAMPLE 3

One preferred manufacturing process is as follows:
1. Synthetic polyisoprene latex is cooled to 15° C.±2° C. and then compounded with the ingredients in Example 1.
2. The compounded synthetic polyisoprene latex is then stored at 15°±2° C. for 24-48 hours until the requisite level of PRM has been reached.
3. The synthetic polyisoprene latex is then transferred to the reserve tank, and maintained at 15° C.±2° C.
4. The synthetic polyisoprene latex is then transferred to the dipping tanks and product dipping started as soon as possible to avoid any further maturation; the latex in the tanks is maintained at a temperature of <15° C.

5. After the first dip, the dipping mandrels with their films are passed through a drying oven.
6. They are then passed through a refrigeration unit to cool the dipping mandrels back down to 15° C.±2° C. so as not to heat the synthetic polyisoprene latex in the second dip tank.
7. After the second dip, the films on the dipping mandrels are dried and vulcanised at about 120° C.-130° C. for about 10 minutes.

The invention claimed is:

1. A process for making a compounded synthetic polyisoprene latex suitable for making a latex film comprising:
   (a) compounding a synthetic polyisoprene latex with suitable compounding ingredients;
   (b) maturing the latex for at least about 24 hours; and optionally
   (c) storing the latex;
   wherein at least the steps (a) and (b) are carried out at a temperature of less than 20° C. so as to minimize prevulcanization of the latex;
   wherein an initial tensile strength of the latex is at least 24 MPa; and
   wherein the suitable compounding ingredients comprise an accelerator consisting of a dithiocarbamate.

2. A process for making a synthetic polyisoprene condom comprising:
   dipping a suitably shaped former into a compounded synthetic polyisoprene latex; and
   vulcanizing the latex to form a condom;
   wherein during preparation, the latex is maintained at a temperature of less than 20° C. so as to minimize prevulcanization of the latex, and the latex is matured for at least about 24 hours resulting in an initial tensile strength of the condom of at least 24 MPa; and
   wherein the compounded synthetic polyisoprene latex comprises an accelerator consisting of a dithiocarbamate.

3. The process according to claim 2, wherein the compounded synthetic polyisoprene latex is prepared by a process comprising:
   (a) compounding a synthetic polyisoprene latex with suitable compounding ingredients;
   (b) maturing the latex; and optionally
   (c) storing the latex.

4. The process according to claim 2, wherein the synthetic polyisoprene latex is maintained at low temperature during compounding of the latex, maturation, storage in the reserve tanks, transfer to the dipping line and so far as possible during dipping, up until the point of vulcanization.

5. The process according to claim 1, wherein the latex is maintained at or cooled to a temperature of about 17° C. or less.

6. The process according to claim 5, wherein the latex is maintained at or cooled to a temperature of about 15° C. or less.

7. The process according to claim 5, wherein the latex is maintained at or cooled to a temperature of about 15° C.±2° C.

8. The process according to claim 7, wherein during all stages prior to vulcanization, the latex is maintained at about 15° C.±2° C.

9. The process according to claim 1, wherein the temperature is such that the prevulcanisate relaxed modulus measurement (PRM) of the latex is about 0.1 MPa or less.

10. The process according to claim 9, wherein the temperature is such that the PRM of the latex is from about 0.08 to 0.10 MPa.

11. The process according to claim 1, wherein the latex is matured for about 24 to about 48 hours.

12. The process according to claim 1, wherein the maturation time is no longer than results in a PRM of the latex of about 0.1 MPa or less.

13. The process according to claim 11, wherein the maturation time is no longer than results in a PRM of about 0.08 to 0.1 MPa.

14. The process according to claim 2, wherein dipping is carried out with no coagulation of the latex.

15. The process according to claim 2, wherein dipping is done at least twice.

16. The process according to claim 14, wherein the latex is cooled between dips.

17. The process according to claim 1, wherein the accelerator consists of zinc dibutyldithiocarbamate.

18. A method for making a latex film article, comprising forming a compounded latex made by a process according to claim 1 into the latex film article.

19. The method according to claim 18, wherein the latex film article is a condom.

20. A process for making a synthetic polyisoprene condom comprising:
   compounding a synthetic polyisoprene latex with one or more suitable compounding ingredients;
   maturing the latex for about 24 hours to about 48 hours to form a condom having at least two of the following initial properties:
      an initial tensile strength of at least 24 MPa;
      an initial burst pressure of at least 1.3 kPa;
      an initial burst volume of at least 44 dm$^3$; and
      an initial elongation-at break value of at least 1000%;
   wherein the compounding and maturing steps are carried out at a temperature of less than 20° C.; and
   wherein the one or more suitable compounding ingredients comprises an accelerator consisting of a dithiocarbamate.

21. The process according to claim 20, wherein the step of maturing the latex forms a condom having at least three of the initial properties.

22. The process according to claim 20, wherein the step of maturing the latex forms a condom having all four of the initial properties.

23. The process according to claim 1, wherein the initial tensile strength of the latex after maturing is at least 28 MPa.

24. The process according to claim 1, comprising maturing the latex for about 24 to about 48 hours.

25. The process according to claim 2, wherein the initial tensile strength of the latex after maturing is at least 28 MPa.

26. The process according to claim 2, wherein the latex is matured for about 24 to about 48 hours.

27. The process according to claim 20, wherein the accelerator consists of zinc dibutyldithiocarbamate.

28. The process according to claim 2, wherein the accelerator consists of zinc dibutyldithiocarbamate.

* * * * *